(12) United States Patent
Tamai (10) Patent No.: US 12,311,154 B2
(45) Date of Patent: May 27, 2025

(54) MEDICAL NEEDLE

(71) Applicant: SB-KAWASUMI LABORATORIES, INC., Kanagawa (JP)

(72) Inventor: Yusuke Tamai, Oita (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 0 days.

(21) Appl. No.: 17/234,881

(22) Filed: Apr. 20, 2021

(65) Prior Publication Data

US 2021/0330895 A1    Oct. 28, 2021

Related U.S. Application Data

(60) Provisional application No. 63/014,737, filed on Apr. 24, 2020.

(51) Int. Cl.
*A61M 5/32* (2006.01)
*A61M 25/06* (2006.01)

(52) U.S. Cl.
CPC ....... *A61M 5/3257* (2013.01); *A61M 25/0612* (2013.01)

(58) Field of Classification Search
CPC .............. A61M 5/3257; A61M 5/3275; A61M 25/0631; A61M 5/3232; A61M 25/0637; A61M 25/0612; A61M 25/0618; A61M 25/0625; A61B 5/150656
See application file for complete search history.

(56) References Cited

U.S. PATENT DOCUMENTS

| | | | |
|---|---|---|---|
| 6,210,371 B1 | 4/2001 | Shaw | |
| 7,097,633 B2* | 8/2006 | Botich | A61B 5/150366 604/110 |
| 2004/0116855 A1* | 6/2004 | Popov | A61M 25/0631 604/110 |
| 2019/0282785 A1 | 9/2019 | Tamai | |

FOREIGN PATENT DOCUMENTS

| | | |
|---|---|---|
| JP | 2002539897 A | 11/2002 |
| JP | 2019155097 A | 9/2019 |

\* cited by examiner

*Primary Examiner* — Emily L Schmidt
(74) *Attorney, Agent, or Firm* — Shih IP Law Group, PLLC.

(57) ABSTRACT

To provide a medical needle capable of preventing malfunction of a movement mechanism at the time of use, and improving safety even further. A medical needle 1A includes: a needle portion 10; a case 20 which is capable of exposing a needle tip of the needle portion 10 from a distal end, and is capable of accommodating the needle portion 10; a movement mechanism M which moves the needle portion 10 inside the case 20; an operation portion 62 for operating the movement mechanism; and an operation regulation portion 80A that regulates operation of the operation portion 62.

9 Claims, 11 Drawing Sheets

MEDICAL NEEDLE

CROSS REFERENCE TO RELATED APPLICATIONS

This application is entitled to and claims the benefit of U.S. provisional application Ser. No. 63/014,737 filed on Apr. 24, 2020, the disclosure of which is incorporated herein by reference in its entirety.

TECHNICAL FIELD

The present invention relates to a medical needle.

BACKGROUND ART

Conventionally, as a medical needle used for blood sampling, blood transfusion, infusion, and the like, a type of medical needle is known that pulls the needle tip into a cylindrical case by using a spring force (for example, see Patent Literatures 1 and 2). In such a conventional medical needle, it is possible to prevent accidents in which users (such as medical workers and the patients themselves) are accidentally punctured by the medical needle after withdrawal of the needle (so-called accidental puncturing). It is also possible to prevent scattering of the blood remaining on the needle tip or inside the needle.

CITATION LIST

Patent Literature

Patent Literature 1: National Publication of International Patent Application No. 2002-539897
Patent Literature 2: Japanese Unexamined Patent Application Publication No. 2019-155097

SUMMARY OF THE INVENTION

Problems to be Solved by the Invention

However, the medical needle disclosed in Patent Literature 2 has a configuration in which the needle tip is pulled inside the case by operating (pressing) an operation portion, which causes a movement mechanism to operate. The needle tip is covered with a cap before use, and in this state, for example, the operation portion is also covered with the cap to prevent malfunction of the movement mechanism. On the other hand, because the cap is detached during use, it is possible to operate the operation portion. If the operation portion is erroneously operated at the time of puncturing or during blood sampling, there is a problem that the movement mechanism malfunctions and causes the needle tip to be accommodated inside the case.

An object of the present invention is to provide a medical needle which is capable of preventing malfunction of the movement mechanism during use, and improving safety even further.

Means of Solving the Problems

A medical needle according to an aspect of the present invention includes: a needle portion; a case which is capable of exposing a needle tip of the needle portion from a distal end, and is capable of accommodating the needle portion; a movement mechanism which moves the needle portion inside the case until the needle tip protruding from the case is accommodated inside the case; an operation portion for operating the movement mechanism, configured to allow a pressing operation in a pressing operation direction perpendicular to a movement direction of the needle portion when the needle portion is moved by the movement mechanism; an operation member which is included in the movement mechanism and in which the operation portion is integrally formed; an operation regulation portion that regulates the pressing operation of the operation portion; and an engaging portion that is engaged with the operation regulation portion in the movement direction of the needle portion and overlaps the operation regulation portion in the pressing operation direction, wherein: the medical needle has an elongated shape in a longitudinal direction in which the needle portion extends, and, in the longitudinal direction, a side to which the needle tip protrudes is a distal end side and a side opposite the side to which the needle tip protrudes is a proximal end side, the case comprises: a first opening which opens in a direction toward the distal end side and from which the needle portion protrudes; a second opening which is provided at an edge portion of the first opening and opens in a same direction as the first opening; and a flat plate-shaped portion which extends from an end of the second opening in the longitudinal direction, the end of the second opening being positioned at an outside with respect to the edge portion in a radial direction of the first opening, an end portion at the distal end of the flat plate-shaped portion is configured to function as the engaging portion and includes a flat surface portion extending in the longitudinal direction at an outside in the radial direction of the end portion at the distal end of the flat plate-shaped portion, an end portion at the distal end of the operation member is provided with the operation portion, and the operation portion is provided with the operation regulation portion at the proximal end side of the operation portion, the operation regulation portion is a notch which is formed to be opened to the proximal end side concave in a U-shape along the movement direction of the needle portion, the notch comprising: a first flat surface which is disposed at an outside with respect to the flat plate-shaped portion in the radial direction and extends in the longitudinal direction; a bottom surface for the U-shape which extends from an end portion at the distal end side of the first flat surface inwardly in the pressing operation direction; and a second flat surface which is disposed at an inside with respect to the flat plate-shaped portion in the radial direction and extends in parallel with the first flat surface in the longitudinal direction from an end portion at the distal end side of the bottom surface toward the proximal end side, and the first flat surface is configured to face the flat surface portion from an outside in the radial direction when the end portion at the distal end side of the flat plate-shaped portion is inserted into the notch from the proximal end side such that the operation regulation portion and the engaging portion are engaged in the movement direction of the needle portion and overlap each other in the pressing operation direction, and the first flat surface and the flat surface portion facing each other are configured to directly contact with each other to regulate the pressing operation.

Effects of the Invention

According to the medical needle of the present invention, it is possible to prevent malfunction of the movement mechanism during use, and to improve safety even further.

MODE FOR CARRYING OUT THE INVENTION

Hereinafter, embodiments of the present invention will be described in detail with reference to the drawings.

In the present embodiments, for example, medical needles 1A and 1B (so-called winged needles), which are used by being secured following puncturing of the patient's skin at the time of blood sampling, blood transfusion, infusion, and the like, will be described as examples of the present invention. The medical needles 1A and 1B have a configuration in which the needle tip is pulled inside a case by using a spring force.

First Embodiment

Figure 1:
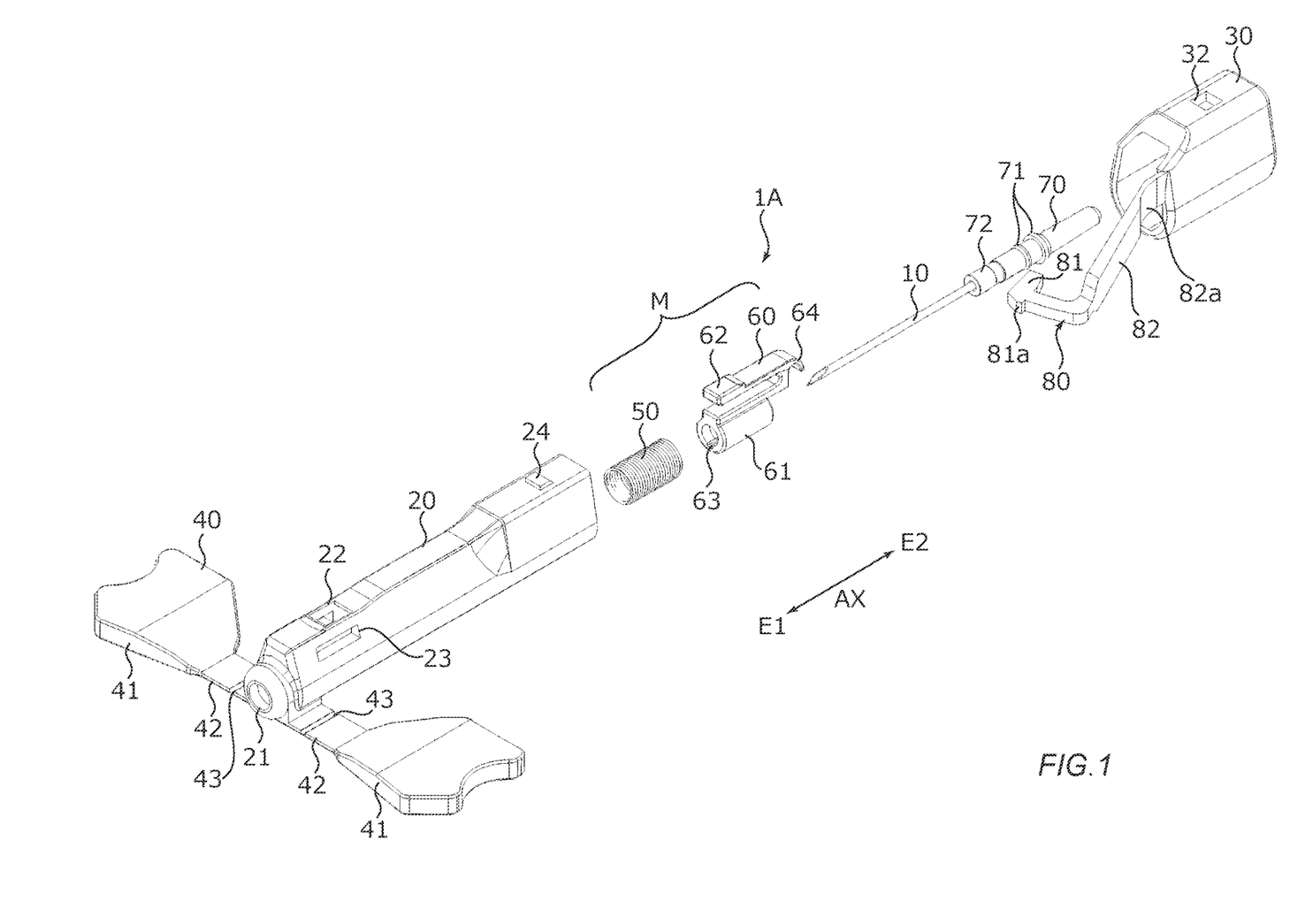
FIG. 1 is an exploded perspective view of a medical needle according to a first embodiment as viewed from the distal end side.
Figure 2:
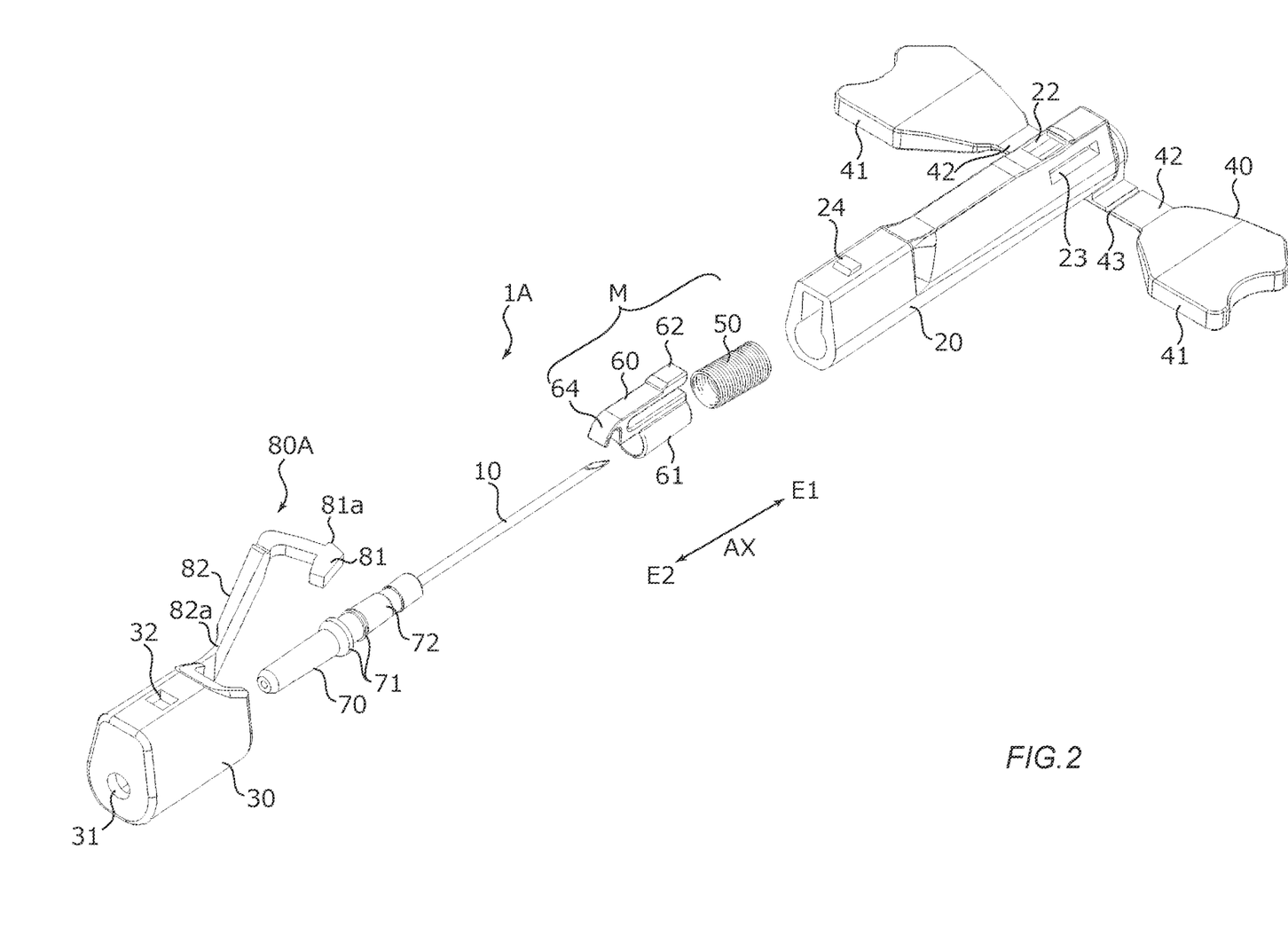
FIG. 2 is an exploded perspective view of the medical needle according to the first embodiment as viewed from the rear end side.

FIG. 1 and FIG. 2 are exploded perspective views of a medical needle 1A according to a first embodiment. In the description below, the side on which the needle tip protrudes in a longitudinal direction AX is referred to as the "distal end E1", and the opposite side is referred to as the "proximal end E2". Furthermore, a state where a predetermined length of the needle tip is protruding from the case 20 is referred to as the "first state". A state where the needle tip is accommodated inside the case 20 is referred to as the "second state".

As shown in FIG. 1 and FIG. 2, the medical needle 1A includes a needle portion 10, a case 20, a cover portion 30, a wing portion 40, a biasing member 50, an operation member 60, a securing portion 70, and an operation regulation portion 80A. A case that accommodates the needle portion 10 is formed by the case 20 and the cover portion 30. Furthermore, the biasing member 50 and the operation member 60 form a movement mechanism M for switching the needle portion 10 from the first state to the second state.

A cap (not shown) is attached to the medical needle 1A before use so as to cover the needle protruding from the case 20. The cap is detachably attached so as to cover, for example, a section of the case 20 on the distal end E1 side (including the upper surface of the operation portion 62).

In the medical needle 1A, the cap, the case 20, the cover portion 30, the wing portion 40, the operation member 60, the securing portion 70, and the operation regulation portion 80A are formed of a plastic material such as polycarbonate or polypropylene.

The needle portion 10 is a hollow needle having a flow path for blood or a drug solution. The needle portion 10 is made of a metallic material such as stainless steel, aluminum, aluminum alloy, titanium, or titanium alloy. The end portion of the needle portion 10 on the proximal end E2 side (the end portion on the opposite side to the needle tip) is secured to the securing portion 70 by adhesion or the like, and is connected to a tube (not shown). The needle portion 10 may be made of a material other than a metallic material, such as a resin material.

The case 20 has a cylindrical shape which is open at both ends, and a space for accommodating the needle portion 10 and the movement mechanism M is formed inside the case 20 along the longitudinal direction AX. For example, a circular opening 21 is provided on the distal end E1 side of the case 20. The diameter of the opening 21 is set slightly larger than the outer diameter of the needle portion 10, and the needle tip is exposed through the opening 21.

A first engaging portion 22 that engages the operation portion 62 of the operation member 60 in the first state is provided on the upper surface of the case 20 on the distal end E1 side. The first engaging portion 22 is, for example, a square hole that communicates with the internal space of the case 20. Furthermore, a second engaging portion 25 that engages with the operation portion 62 of the operation member 60 in the second state is provided on the inner surface of the case 20 on the proximal end E2 side (see FIG. 4B). The second engaging portion 25 is, for example, a step provided on the inner surface of the case 20.

Insertion slits 23 for displaceably inserting the operation regulation portion 80A into the case 20 are provided on both side surfaces of the case 20 on the distal end E1 side. Furthermore, locking portions 24 for maintaining an engaged state with the cover portion 30 are provided on the upper surface and the lower surface of the case 20 on the proximal end E2 side.

The cover portion 30 is a lid member that closes the opening on the proximal end E2 side of the case 20. An opening 31 for passing a tube (not shown) connected to the needle portion 10 is provided at the end portion of the cover portion 30 on the proximal end E2 side. Furthermore, the inner surface of the end portion is provided with a concave portion 33 into which an impact mitigating portion 64 of the operation member 60 enters in the second state (see FIG. 4A and the like). Moreover, the upper surface and the lower surface of the cover portion 30 are provided with engagement holes 32 that engage with the locking portions 24 of the case 20.

The wing portion 40 is a pair of wing members extending on both sides of the distal end of the case 20, and, for example, is integrally formed with the case 20. The wing portion 40 includes a grip portion 41, and a thin-walled portion 42 formed thinner than the grip portion 41. The grip portion 41 is configured to be rotatable by a predetermined angle about a groove 43 formed in the thin-walled portion 42.

The biasing member 50 is a member that exerts a biasing force to an extent that causes the operation member 60 to be pressed against the proximal end E2 side of the cover portion 30 in the second state. The biasing member 50 is, for example, configured by a metallic compression coil spring, and is arranged on a section 72 on the distal end E1 side of the securing portion 70.

The operation member 60 includes a joint portion 61 and an operation portion 62.

The joint portion 61 has, for example, a circular tube shape. The inner surface of the joint portion 61 on the distal end E1 side is formed having a smaller diameter than the section on the proximal end E2 side, and a groove 63 is provided along the longitudinal direction AX.

The operation portion 62 is an operation lever for releasing the engagement between the case 20 and the operation member 60 (movement mechanism M) when the needle portion 10 is accommodated inside the case 20. The operation portion 62 is, for example, arranged on the outer surface of the joint portion 61, and is formed in a substantially letter-U shape along the longitudinal direction AX. The free end of the operation portion 62 has a bulging shape that can engage with the first engaging portion 22 and the second engaging portion 25 of the case 20.

The operation portion 62 functions as a leaf spring that bends in response to an external force applied to the free end, and exerts a restoring force (biasing force). The operation portion 62 is provided, for example, so that the separation distance from the joint portion 61 increases from the base of the letter-U shape toward the free end. As a result, when the operation member 60 is arranged inside the case 20, an upward biasing force is generated in the operation portion 62, and the engaged state with the first engaging portion 22 or the second engaging portion 25 is maintained. On the other hand, in the first state, when the operation portion 62 is downwardly pressed against the biasing force, the engaged state with the first engaging portion 22 is released.

Further, an impact mitigating portion 64 for mitigating the impact when switching from the first state to the second state is provided on the proximal end E2 side of the operation portion 62. The impact mitigating portion 64 is formed, for example, having a curved shape that hangs down from the end portion of the operation portion 62 on the proximal end E2 side. The impact mitigating portion 64 absorbs an impact by becoming more curved when a force greater than or equal to a predetermined force is applied.

The securing portion 70 is, for example, a circular tubular member into which the end portion of the needle portion 10 on the proximal end E2 side is inserted and secured. The outer surface of the securing portion 70 is provided with two flange portions 71, which are arranged side by side at a substantially central position in the longitudinal direction. Furthermore, a ridge (reference numeral omitted) that corresponds to the groove 63 of the joint portion 61 is provided along the longitudinal direction AX on the lower side of outer surface of the securing portion 70.

The securing portion 70 is inserted into the joint portion 61 of the operation member 60 from the proximal end E2 side. The securing portion 70 is inserted while engaging the ridge with the groove 63 of the joint portion 61. A small-diameter section of the joint portion 61 is fitted between the two flange portions 71 as a result of the flange portion 71 on the distal end E1 side being pushed in until it clears the end surface of the joint portion 61 on the proximal end E2 side. Furthermore, the biasing member 50 is attached to the section 72 of the securing portion 70 which is exposed from the joint portion 61.

The operation regulation portion 80A regulates pressing operations made with respect to the operation portion 62. In the present embodiment, the operation regulation portion 80A includes an arm 82, which protrudes in a letter-L shape from the end portion of the cover portion 30 on the distal end E1 side, and a head 81 provided on the free end of the arm 82. The head 81 and a section of the arm 82 on the head 81 side are inserted into the case 20 from the insertion slit 23. In the present embodiment, the operation regulation portion 80A is integrally formed with the cover portion 30.

In a state where the medical needle 1A is assembled, the head 81 is a section which is located between the joint portion 61 and the operation portion 62 of the operation member 60. The head 81 includes a slit engaging portion 81a, and the edge of the insertion slit 23 and the slit engaging portion 81a become engaged when the head 81 is press-fitted into the insertion slit 23 of the case 20.

The arm 82 includes a spring portion 82a that functions as a leaf spring on the section which is connected to the cover portion 30. The spring portion 82a bends in response to an external force applied to the arm 82, and exerts a restoring force (biasing force). The spring portion 82a is formed, for example, by bending the distal end E1 side of the arm 82 so that it becomes separated from the case 20. As a result, when the arm 82 is pressed toward the case 20 side, a biasing force is generated in the opposite direction to the pressing direction.

For example, the medical needle 1A is assembled as follows. First, the movement mechanism M comprising the biasing member 50 and the operation member 60 is attached to the needle portion 10. Specifically, the operation member 60 and the biasing member 50 are inserted through from the needle tip in a state where the needle portion 10 is secured by the securing portion 70. Then, the needle portion 10, the securing portion 70, and the movement mechanism M are inserted into the case 20 so that the needle tip protrudes from the opening 21, and press-fitted up to a position where the first engaging portion 22 of the case 20 and the operation portion 62 of the operation member 60 become engaged. Then, the cover portion 30 is attached to the proximal end E2 side of the case 20.

The first state is maintained as a result of the first engaging portion 22 of the case 20 and the operation portion 62 of the operation member 60 being engaged. At this time, the biasing member 50 is arranged in a state where it is compressed in the internal space of the case 20. The edge of the biasing member 50 on the distal end E1 side makes contact with the inner surface of the case 20 on the distal end side, and the edge on the proximal end E2 side makes contact with the end surface of the operation member 60 on the distal end E1 side (see FIG. 4B).

Figure 3A:
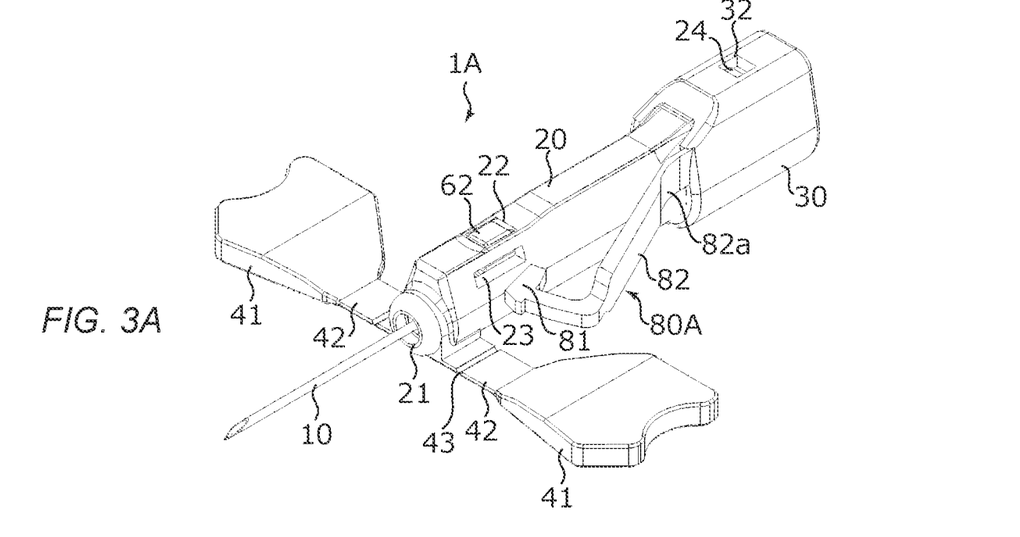
FIGS. 3A and 3B are perspective views showing a state of the medical needle after assembling each of the members.
Figure 3B:
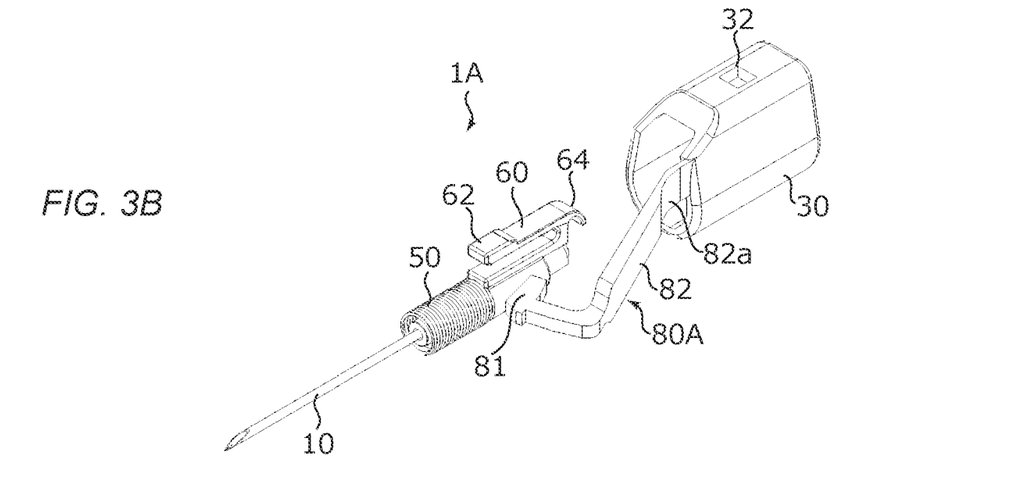
Figure 4A:
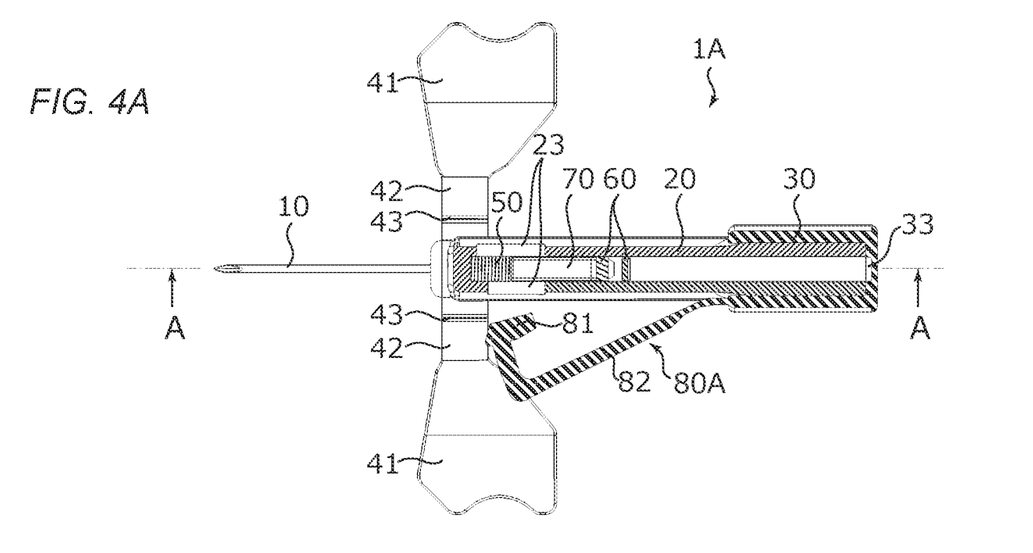
FIGS. 4A and 4B are cross-sectional views showing a state of the medical needle after assembling each of the members.
Figure 4B:
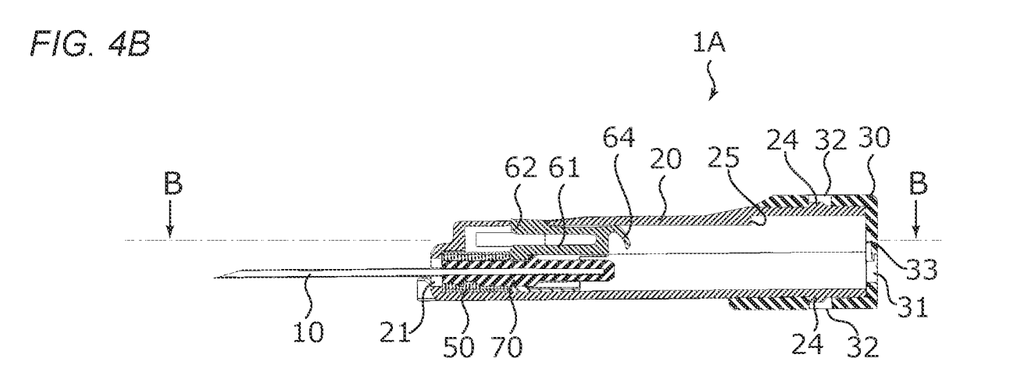

The state of the medical needle 1A after assembling each of the members as described above is shown in FIG. 3A, FIG. 3B, FIG. 4A, and FIG. 4B. FIG. 3A and FIG. 3B are perspective views of the medical needle 1A. FIG. 3B omits the case 20 and the wing portion 40. Furthermore, FIG. 4A is a cross-sectional view taken along line B-B in FIG. 4B. FIG. 4B is a cross-sectional view taken along line A-A in FIG. 4A.

After assembling each of the members, the arm 82 is in an unloaded state. As a result, the operation regulation portion 80A is arranged outside the case 20 as shown in FIG. 3A and the like. In this state, the arm 82 is pressed toward the case 20 side, and the head 81 is press-fitted into the insertion slit 23 due to a change in shape of the arm 82.

Figure 5A:
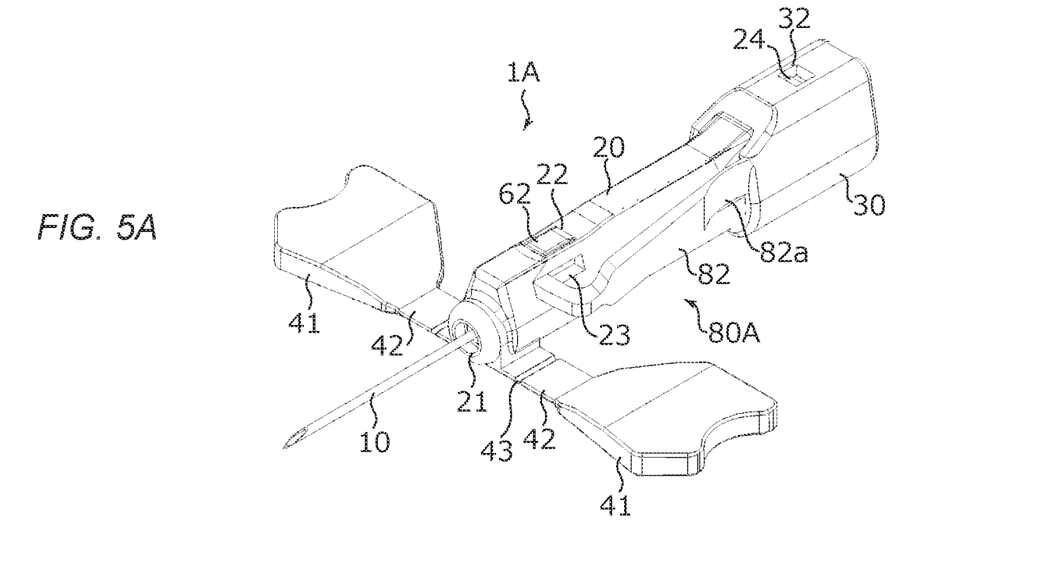
FIGS. 5A and 5B are perspective views showing a state of the medical needle after the operation regulation portion is press-fitted inside the case.
Figure 5B:
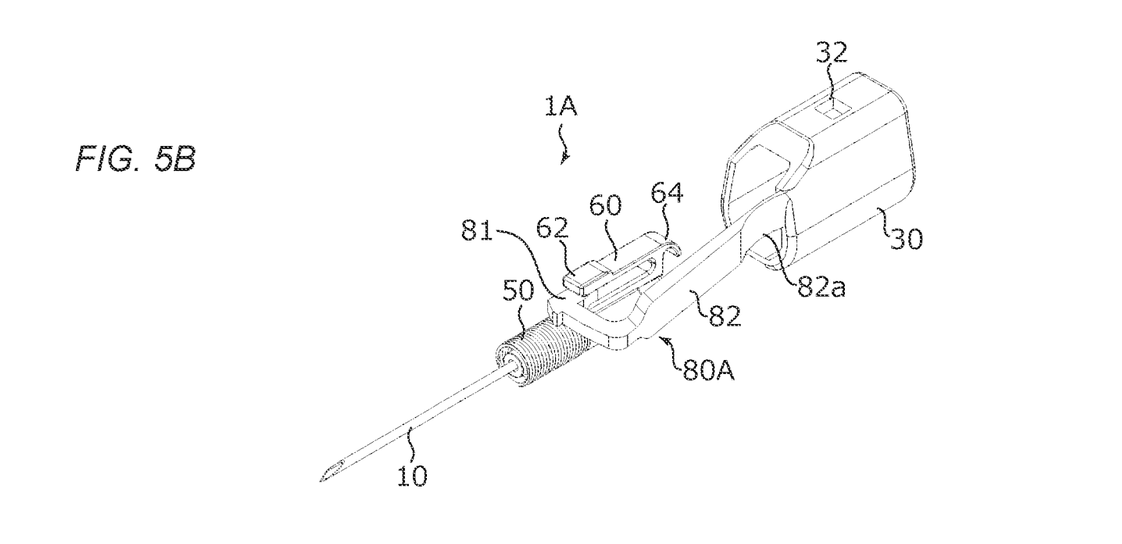
Figure 6A:
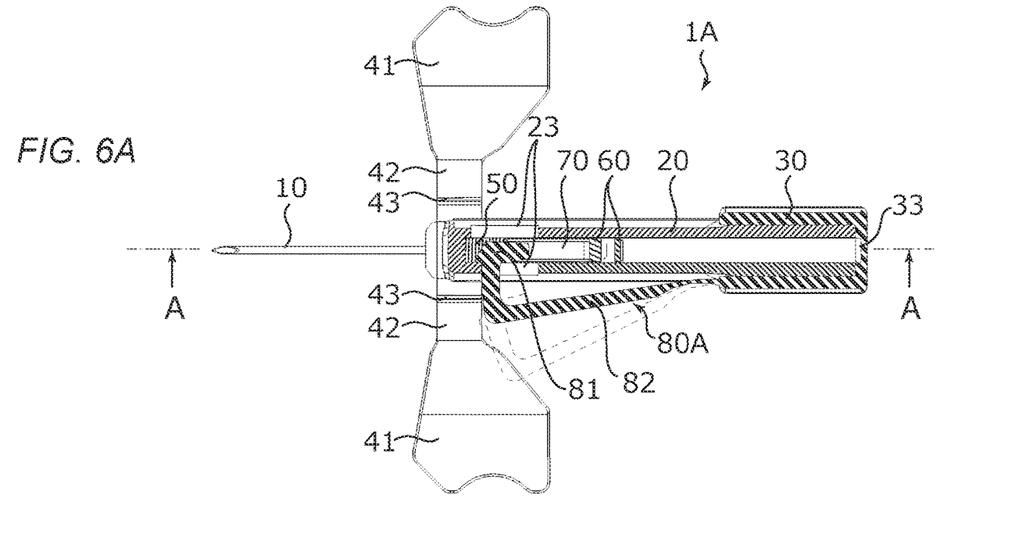
FIGS. 6A and 6B are cross-sectional views showing a state of the medical needle after the operation regulation portion is press-fitted inside the case.
Figure 6B:
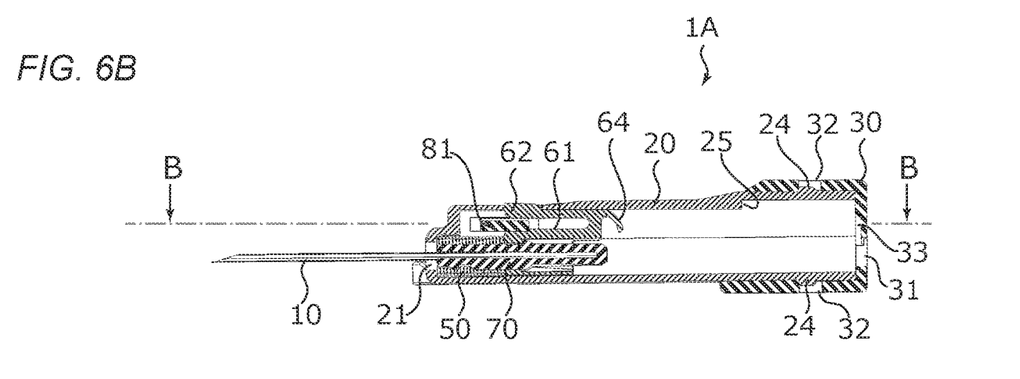

The state of the medical needle 1A after press-fitting the operation regulation portion 80A inside the case 20 is shown in FIG. 5A, FIG. 5B, FIG. 6A, and FIG. 6B. FIG. 5A and FIG. 5B are perspective views of the medical needle 1A. FIG. 5B omits the case 20 and the wing portion 40. Furthermore, FIG. 6A is a cross-sectional view taken along line B-B in FIG. 6B. FIG. 6B is a cross-sectional view taken along line A-A in FIG. 6A.

After press-fitting the operation regulation portion 80A, the arm 82 is in a state where it is biased in the opposite direction to the pressing direction. As a result, the operation regulation portion 80A tries to restore a state where the arm 82 is not press-fitted (such as FIG. 3A). However, because the slit engaging portion 81a of the head 81 engages with the edge of the insertion slit 23 of the case 20, further restoration is inhibited, and the state in which the operation regulation portion 80A is press-fitted inside the case 20 is maintained. At this time, the head 81 is downwardly positioned in the displacement direction of the operation portion 62, that is to say, between the operation portion 62 and the joint portion 61, and pressing operations made with respect to the operation portion 62 are regulated. Furthermore, the arm 82 is in a state where it is separated from the case 20, and the regulation by the operation portion 62 can be released by pressing the arm 82 further toward the case 20 side. That is to say, the operation regulation portion 80A is configured so as to be capable of switching between regulation of operation of the operation portion 62, and releasing of the regulation.

The state shown in FIG. 5A and the like is the initial state of the medical needle 1A. The medical needle 1A is stored by attaching a cap to the needle tip when not in use. When the medical needle 1A is used, the cap is detached to expose the needle tip. Then, the patient's skin is punctured by the needle portion 10 while the grip portion 41 of the wing portion 40 is being gripped. After the puncture is made, the grip portion 41 is expanded and taped down as necessary.

At this time, although the operation portion 62 is exposed, pressing operations are disabled by the operation regulation portion 80A. Therefore, at the time of use, it is possible to reliably prevent the operation portion 62 from being pressed and the movement mechanism M from malfunctioning, against the user's intent.

Figure 7A:
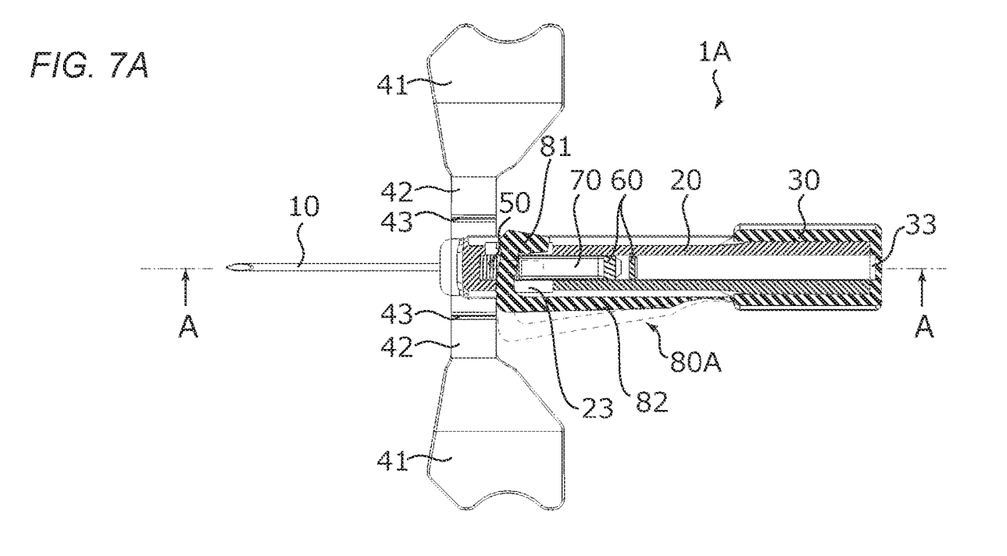
FIGS. 7A and 7B are cross-sectional views showing a state after operation regulation of the medical needle is released.
Figure 7B:
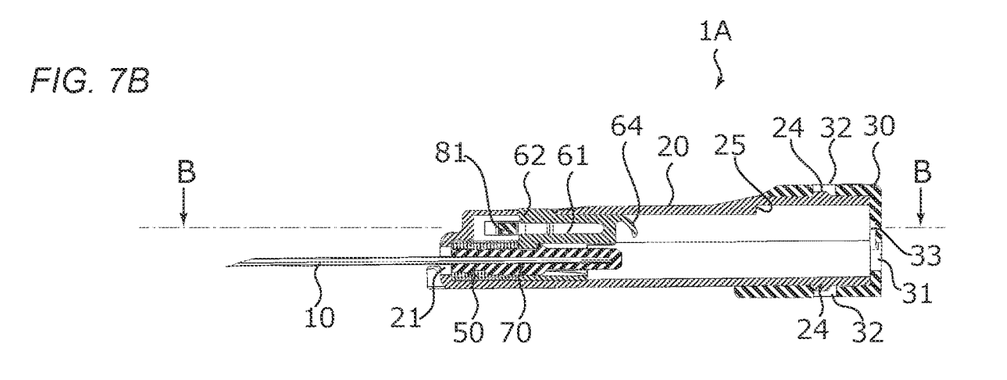

When the needle tip is withdrawn from the patient's skin, the operation regulation of the operation regulation portion 80A is released. Specifically, as shown in FIG. 7A and FIG. 7B, the arm 82 is pressed toward the case 20 side, and the head 81 is shifted to a position which is displaced from below the operation portion 62. As a result, pressing operations can be made with respect to the operation portion 62.

Figure 8A:
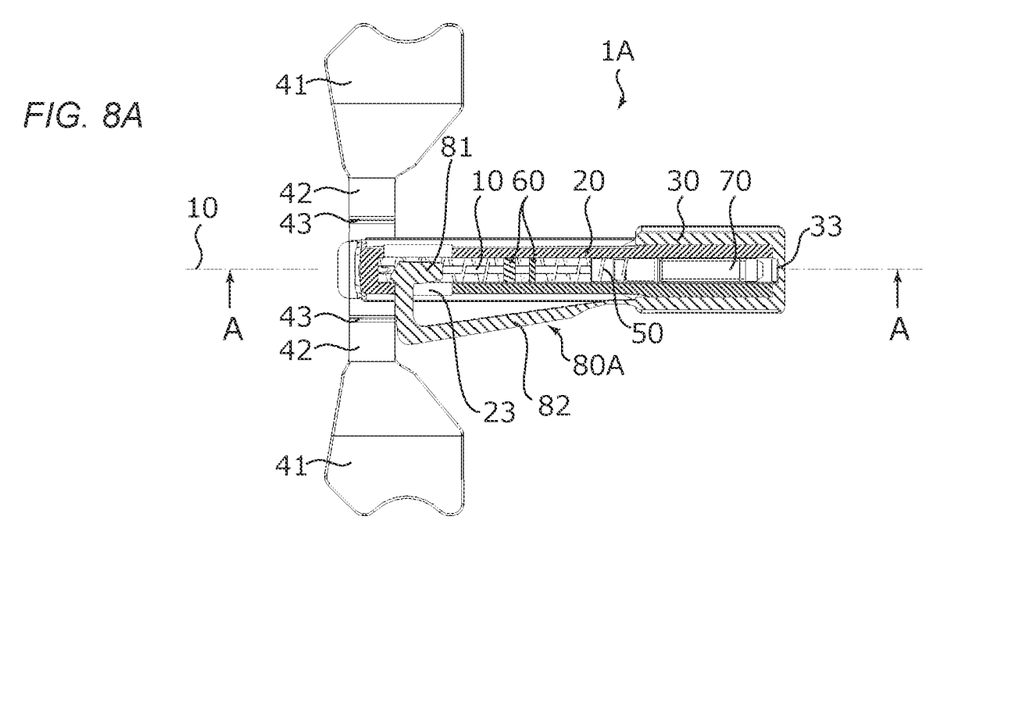
FIGS. 8A and 8B are cross-sectional views showing a state of the medical needle after accommodating the needle portion.
Figure 8B:
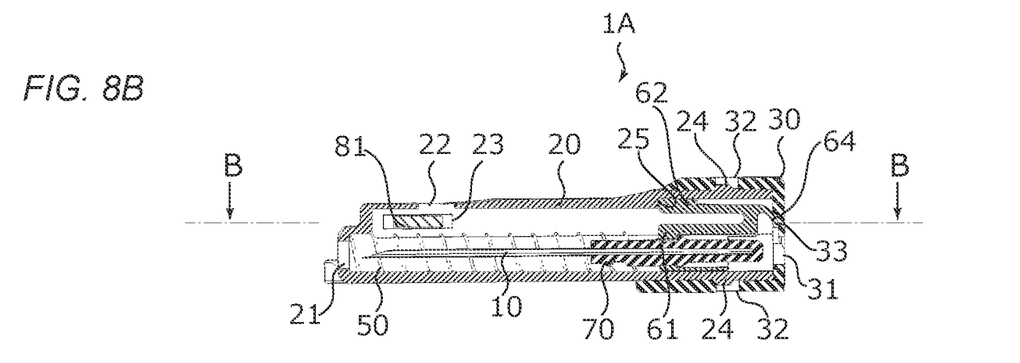

When the operation portion 62 of the operation member 60 is pressed in this state, as shown in FIG. 8A and FIG. 8B, the movement mechanism M operates due to the action of the biasing member 50, and the operation member 60, the securing portion 70, and the needle portion 10 move toward the proximal end E2 side. As a result, the needle tip which is exposed from the case 20 is accommodated inside the case 20. Therefore, it is possible to prevent accidental puncturing after withdrawal of the needle, and scattering of the blood remaining on the needle tip or inside the needle portion 10.

At this time, the action of the impact mitigating portion 64 mitigates the impact caused by the contact between the impact mitigating portion 64 and the cover portion 30, and the generation of collision noises is also suppressed. Furthermore, the operation regulation portion 80A returns to a state which is equivalent to the initial state shown in FIG. 5A and the like.

Note that the needle portion 10 may be accommodated inside the case 20 by pressing the operation portion 62 after the needle tip has firstly been withdrawn from the patient's skin.

Second Embodiment

Figure 9:
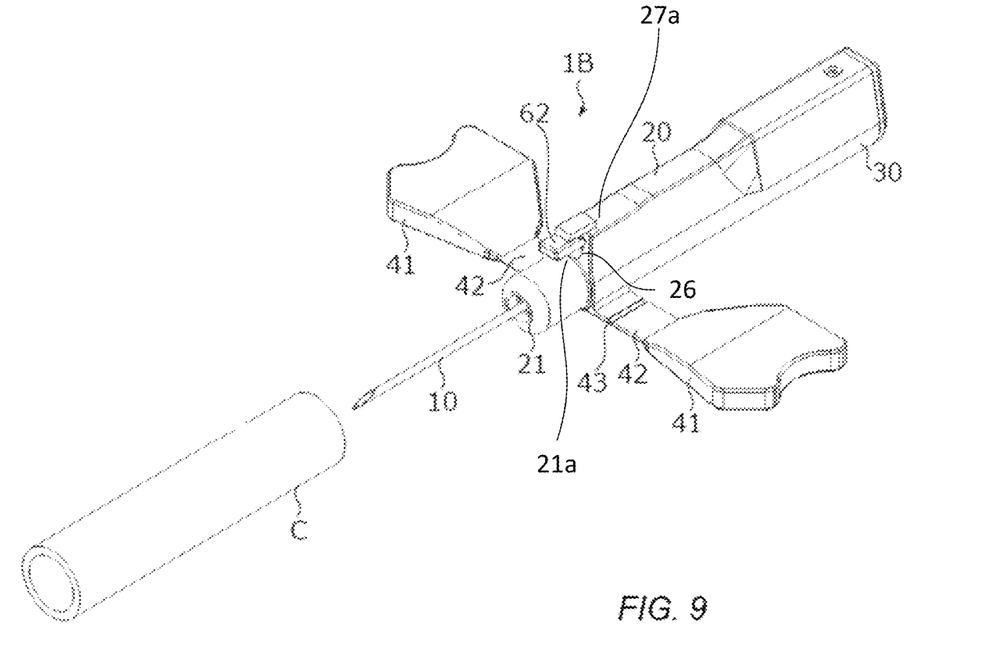
FIG. 9 is a perspective view of a medical needle according to a second embodiment.
Figure 10A:
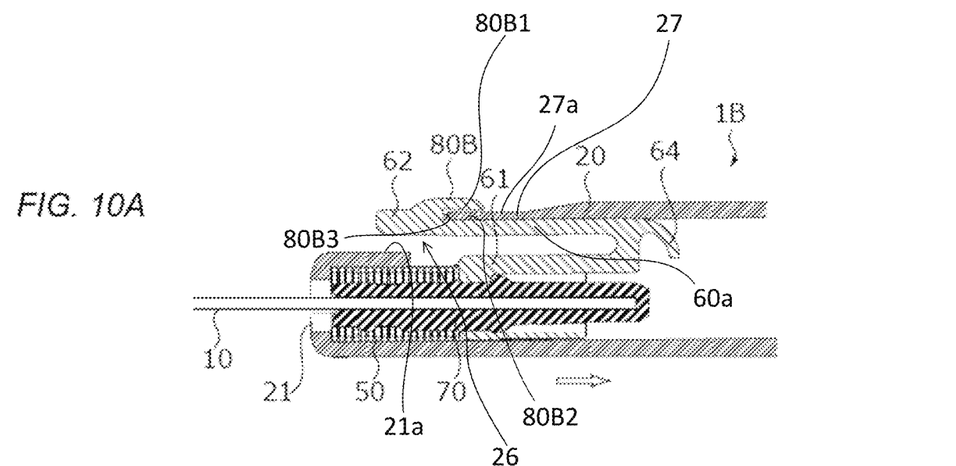
FIGS. 10A and 10B are cross-sectional views of the main parts of the medical needle according to the second embodiment.
Figure 10B:
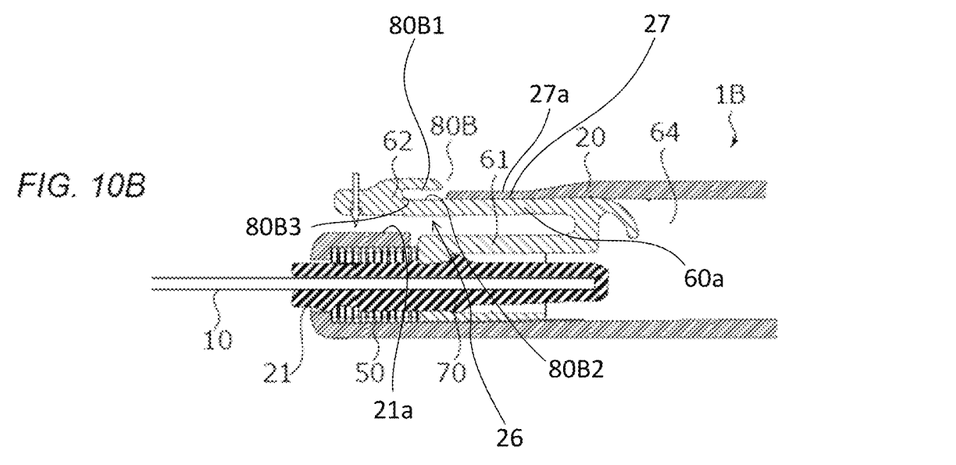

FIG. 9 is a perspective view of a medical needle 1B according to a second embodiment. FIGS. 10A and 10B are cross-sectional views of the main parts of the medical needle 1B. FIG. 10A shows a state where operation of the operation portion 62 is regulated. FIG. 10B shows a state where the operation regulation of the operation portion 62 is released. In the medical needle 1B, the configurations of the operation portion and the operation regulation portion are different to those of the medical needle 1A according to the first embodiment; and the rest of the configuration is substantially equivalent to the medical needle 1A. That is to say, the medical needle 1B includes a needle portion 10, a case 20, a cover portion 30, a wing portion 40, a biasing member 50, an operation member 60, a securing portion 70, and an operation regulation portion 80B.

In the medical needle 1B, the operation portion 62 is arranged such that it protrudes from the case 20 toward the distal end E1 side. Before use, the rear end portion of a cap C, which is attached so as to cover the needle tip, enters between the operation portion 62 and the distal end portion of the case 20 (the section provided with the opening 21), which regulates pressing operations made with respect to the operation portion 62.

Furthermore, the operation regulation portion 80B is formed on the end portion of the operation portion 62 on the proximal end E2 side so as to extend in a letter-J shape. In the first state, the operation portion 62 is biased toward the proximal end E2 side. Further, the operation regulation portion 80B engages with the edge of the case 20. At this time, a space is provided between the end surface of the joint portion 61 on the distal end E1 side and the end surface of the distal end portion of the case 20 so that the operation portion 62 can be relatively moved toward the distal end E1 side (and the case 20 toward the proximal end E2 side). As a result, the biasing member 50 is in a state where it is capable of being compressed even more.

In the medical needle 1B, for example, by moving the case 20 toward the proximal end E2 side and relatively moving the operation portion 62 toward the distal end E1 side with respect to the case 20, the engagement between the operation portion 62 and the case 20 is released, and the operation portion 62 is in pressable state (see FIG. 10B). Furthermore, in the medical needle 1B, the operation regulation of the operation portion 62 can be carried out with a simpler structure than that of the medical needle 1A of the first embodiment.

As described above, the medical needles 1A and 1B each include: a needle portion 10; a case 20 which is capable of exposing the needle tip of the needle portion 10 from the distal end E1, and is capable of accommodating the needle portion 10 inside the case 20; a movement mechanism M which moves the needle portion 10 inside the case 20 until the needle tip protruding from the case 20 is accommodated inside the case 20; an operation portion 62 for operating the movement mechanism M; and operation regulation portions 80A and 80B that regulate operation of the operation portion 62.

According to the medical needles 1A and 1B, operation of the operation portion 62 is regulated by the operation regulation portions 80A and 80B. More specifically, even in a state where the cap C has been detached and the needle tip of the needle portion 10 is protruding from the case 20, operation of the operation portion 62 is regulated by the operation regulation portions 80A and 80B. Consequently, the operation portion 62 cannot be easily operated regardless of the presence or absence of the cap C. Consequently, malfunction of the movement mechanism M that moves the needle portion 10 during use can be prevented, and the safety can be improved even further.

Furthermore, the operation regulation portions 80A and 80B are configured so as to be capable of switching between regulation of operation of the operation portion 62, and releasing of the regulation. As a result, the state in which operation of the operation portion 62 is regulated can be easily released. Therefore, the movement mechanism M can be operated without requiring complicated operations.

Moreover, the operation portion 62 causes the movement mechanism M to operate due to an operation to displace from a predetermined position. Further, the operation regulation portions 80A and 80B are located in a displacement direction of the operation portion 62, and regulate the displacement of the operation portion 62. As a result, operation of the operation portion 62 is physically regulated. Therefore, malfunction of the movement mechanism M during use can be reliably prevented.

The invention made by the present inventors has been specifically described above based on the embodiments. However, the present invention is not limited to the above embodiments, and can be changed without departing from the spirit of the present invention.

(Modifications)

Figure 11A:
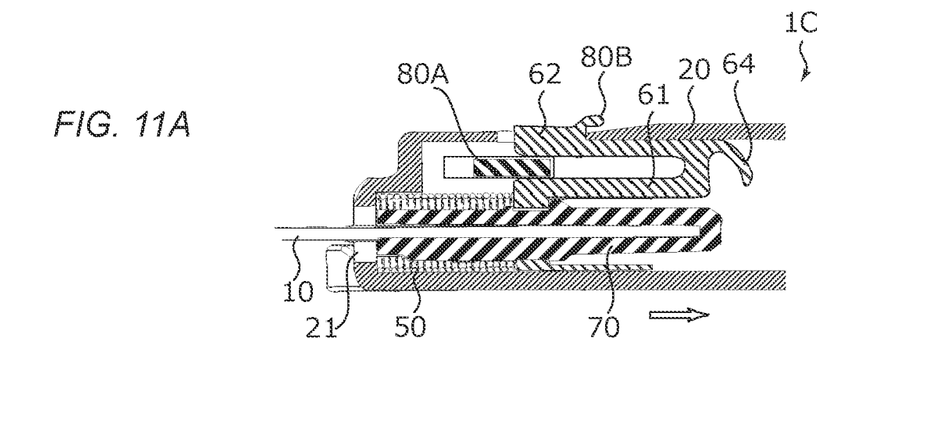
FIGS. 11A and 11B are cross-sectional views of the main parts of a medical needle according a modification.
Figure 11B:
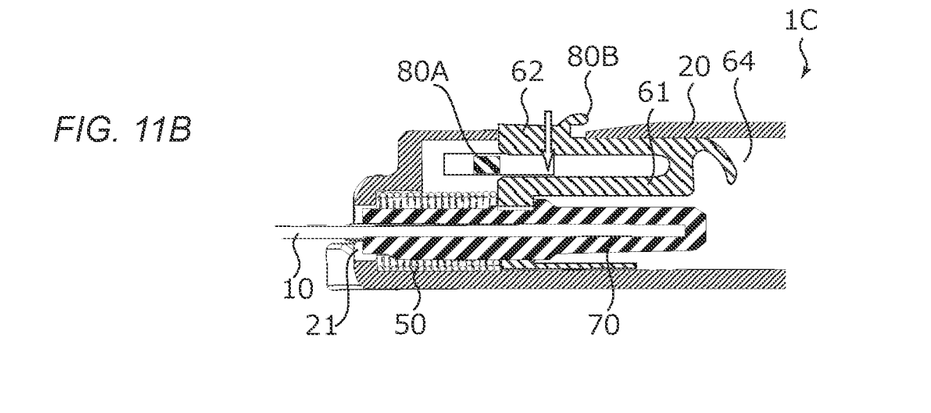

FIGS. 11A and 11B are cross-sectional views of the main parts of a medical needle 1C according to a modification of the first embodiment. FIG. 11A shows a state where operation of the operation portion 62 is regulated. FIG. 11B shows a state where an operation regulation of the operation portion 62 is released.

In the medical needle 1C, the operation regulation portion 80B according to the second embodiment is provided in addition to the operation regulation portion 80A according to the first embodiment, and operation regulation of the operation portion 62 is carried out in two stages. That is to say, in the medical needle 1C, the arm 82 is pressed toward the case 20 side, and the head 81 is shifted to a position which is displaced from below the operation portion 62. In addition, the operation portion 62 is in a pressable state only after the case 20 has been moved toward the proximal end E2 side (see FIG. 11B). Therefore, in the medical needle 1C according to the modification, malfunction of the movement mechanism M during use can be more reliably prevented.

Furthermore, for example, the operation regulation portion is not limited to the configurations described in the embodiments and in the modification, and a rotary lock mechanism may be used.

Moreover, the operation regulation portion may have any function that regulates operation of the operation portion. For example, the regulated state may be released as a result of a pressing force of the operation portion, for example by way of a bubble wrap material. In addition, for example, the operation regulation portion may be configured such that it cannot be easily operated by increasing the rigidity of the operation portion itself.

Furthermore, in the above embodiments, cases have been illustrated and described where a compression coil spring is used as the biasing member 50, and the compression coil spring is arranged on the distal end E1 side of the operation member 60. However, for example, a tension coil spring may be arranged on the proximal end E2 side of the operation member 60. Also, as the biasing member 50, rubber or the like may be applied instead of a spring.

In the above embodiments, a winged needle which is used by being secured following puncturing of a patient's skin has been illustrated and described. However, the present invention is not limited to this. For example, the present invention can be applied to an indwelling needle or the like used when carrying out a continuous intravenous drip infusion.

The embodiments disclosed above are to be considered illustrative in all respects, and are not intended to be restrictive. The scope of the present invention is defined by the scope of claims, and not by the description above. It is intended that all modifications that fall within the meaning and scope equivalent to the scope of claims be included.

DESCRIPTION OF REFERENCE NUMERALS 1A, 1B, 1C Medical needle
10 Needle portion
20 Case
50 Biasing member
60 Operation member
62 Operation portion
70 Securing portion
80A, 80B Operation regulation portion
M Movement mechanism
21a Edge portion
26 Second opening
27 Flat plate-shaped portion
27a Flat surface portion
60a Plate-shaped portion
80B1 First flat surface
80B2 Second flat surface
80B3 Bottom surface

What is claimed is:
1. A medical needle, comprising:
a needle portion;
a case which is capable of exposing a needle tip of the needle portion from a distal end, and is capable of accommodating the needle portion;
a movement mechanism which moves the needle portion inside the case until the needle tip protruding from the case is accommodated inside the case;
an operation portion for operating the movement mechanism, configured to allow a pressing operation in a pressing operation direction perpendicular to a movement direction of the needle portion when the needle portion is moved by the movement mechanism;
an operation member which is included in the movement mechanism and in which the operation portion is integrally formed;
an operation regulation portion that regulates the pressing operation of the operation portion; and
an engaging portion that is engaged with the operation regulation portion in the movement direction of the needle portion and overlaps the operation regulation portion in the pressing operation direction,
wherein:
the medical needle has an elongated shape in a longitudinal direction in which the needle portion extends, and, in the longitudinal direction, a side to which the needle tip protrudes is a distal end side and a side opposite the side to which the needle tip protrudes is a proximal end side,
the case comprises:
a first opening which opens in a direction toward the distal end side and from which the needle portion protrudes;

a second opening which is provided at an edge portion of the first opening and opens in a same direction as the first opening; and a flat plate-shaped portion which extends from an end of the second opening in the longitudinal direction, the end of the second opening being positioned at an outside with respect to the edge portion in a radial direction of the first opening, an end portion at the distal end of the flat plate-shaped portion is configured to function as the engaging portion and includes a flat surface portion extending in parallel with the longitudinal direction at an outside in the radial direction of the end portion at the distal end of the flat plate-shaped portion, an end portion at the distal end of the operation member is provided with the operation portion, and the operation portion is provided with the operation regulation portion at the proximal end side of the operation portion, the operation regulation portion is a notch which is formed to be opened to the proximal end side and to be concave in a U-shape along the movement direction of the needle portion, the notch comprising:
  a first flat surface which is disposed at an outside with respect to the flat plate-shaped portion in the radial direction and extends in parallel with the longitudinal direction;
  a bottom surface for the U-shape which extends from an end portion at the distal end side of the first flat surface radially inwardly in the pressing operation direction; and
  a second flat surface which is disposed at an inside with respect to the flat plate-shaped portion in the radial direction and extends in parallel with the first flat surface in the longitudinal direction from an end portion at the distal end side of the bottom surface toward the proximal end side, and the first flat surface is configured to face the flat surface portion from an outside in the radial direction when the end portion at the distal end side of the flat plate-shaped portion is inserted into the notch from the proximal end side such that the operation regulation portion and the engaging portion are engaged in the movement direction of the needle portion and overlap each other in the pressing operation direction, and the first flat surface and the flat surface portion facing each other are configured to directly contact with each other to regulate the pressing operation.

2. The medical needle according to claim 1, wherein the operation regulation portion and the engaging portion are configured so as to be capable of switching between regulation of the pressing operation of the operation portion, and releasing of the regulation of the pressing operation of the operation portion.

3. The medical needle according to claim 1, wherein the operation portion causes the movement mechanism to operate due to the pressing operation of the operation portion to displace from a predetermined position, and the operation regulation portion and the engaging portion are located in a displacement direction of the operation portion, and regulate the displacement of the operation portion.

4. The medical needle according to claim 1, wherein the operation regulation portion and the engaging portion regulate the pressing operation of the operation portion in a state where the needle tip is protruding from the case.

5. The medical needle according to claim 1, wherein:
the movement mechanism includes a biasing member that biases the operation member toward the proximal end side to maintain the engagement of the operation regulation portion and the engaging portion by a force of the biasing member.

6. The medical needle according to claim 5, wherein:
the biasing member is disposed between an inner surface of the case on the distal end side and a surface of the operation member on the distal end side,
the operation member is movable toward the distal end side relative to the case against the force of the biasing member and configured to cause release of the engagement of the operation regulation portion and the engaging portion to cause release of the regulation of the pressing operation of the operation portion by the operation regulation portion when the operation member moves toward the distal end side.

7. The medical needle according to claim 1, further comprising, a securing portion that is separate from the operation member and to which the needle portion is secured, wherein
the operation member is disposed on an outer circumference of the securing member and moves integrally with the securing member.

8. The medical needle according to claim 1, wherein the operation member is configured to cause release of the regulation of the pressing operation of the operation portion by the operation regulation portion when the operation member moves toward the distal end side to cause withdrawal of the end portion at the distal end side of the flat plate-shaped portion from the notch and cause release of the engagement of the operation regulation portion and the engaging portion.

9. The medical needle according to claim 1, wherein:
the operation member has a plate-shaped portion which extends continuously to the second flat surface and in a same direction as the second flat surface, and
the plate-shaped portion is configured such that, in an engagement state where the operation regulation portion and the engaging portion are engaged, an entirety of a surface at an outer side in the radial direction in the plate-shaped portion contacts a surface at an inner side in the radial direction in the flat plate-shaped portion.

* * * * *